United States Patent [19]

Levesque et al.

[11] Patent Number: 5,531,726

[45] Date of Patent: Jul. 2, 1996

[54] SPHAGNUM MOSS COMPOSITION FOR THE PRODUCTION OF SHEETED ABSORBENT AND METHOD FOR EVALUATING THE POTENTIAL OF SPHAGNUM MOSS MATERIAL FOR ABSORBING LIQUID

[75] Inventors: Yvon Levesque, Montreal; Sylvaine Cote, St-Gédéon; Denis Gallagher, Jonquiere, all of Canada

[73] Assignee: Johnson & Johnson, Inc., Montreal, Canada

[21] Appl. No.: 124,907

[22] Filed: Sep. 21, 1993

[51] Int. Cl.⁶ .............................. A61F 13/15; A61F 13/20
[52] U.S. Cl. ........................ 604/367; 604/358; 604/378; 604/385.1
[58] Field of Search ........................... 604/358, 367–369, 604/378–380, 383, 385.1

[56] References Cited

U.S. PATENT DOCUMENTS

| | | |
|---|---|---|
| 3,673,095 | 6/1972 | Archer . |
| 3,976,074 | 8/1976 | Fitzgerald et al. ............... 604/378 |
| 4,170,515 | 10/1979 | LaLancette et al. . |
| 4,215,692 | 8/1980 | Levesque . |
| 4,226,237 | 10/1980 | Levesque . |
| 4,473,440 | 9/1984 | Ovans . |
| 4,507,122 | 3/1985 | Levesque . |
| 4,704,818 | 11/1987 | Cameon . |
| 4,825,592 | 5/1989 | Earls . |
| 4,920,695 | 5/1990 | Garden . |
| 5,053,029 | 10/1991 | Yang . |
| 5,057,227 | 10/1991 | Cohen . |
| 5,122,407 | 6/1992 | Yeo et al. . |
| 5,167,654 | 12/1992 | Yang . |
| 5,217,448 | 6/1993 | Glaug . |

FOREIGN PATENT DOCUMENTS

| | | |
|---|---|---|
| 2134793 | 8/1984 | United Kingdom . |
| 2134781 | 8/1984 | United Kingdom . |
| 2134791 | 8/1984 | United Kingdom . |
| 2134792 | 8/1984 | United Kingdom . |
| 2135165 | 8/1984 | United Kingdom . |

OTHER PUBLICATIONS

The Dispensatory of the United States of America, 25th Ed. (1955), p. 1868.
George E. Nichols, Sphagnum Moss: War Substitute for Cotton in Absorbent Surgical Dressings, Annual Smithsonian Report (1918), pp. 221–234.

Primary Examiner—Randall L. Green
Assistant Examiner—P. Zuttarelli
Attorney, Agent, or Firm—James P. Barr

[57] ABSTRACT

An absorbent product containing sphagnum moss selected from the group of botanical sections consisting of PALUSTRIA, ACUTIFOLIA, RIGIDA, SUBSECUNDA and CUSPIDATA. The invention also extends to a novel method for manufacturing a highly absorbent structure and to a method for evaluating the liquid absorbent properties of a sphagnum moss composition.

20 Claims, 2 Drawing Sheets

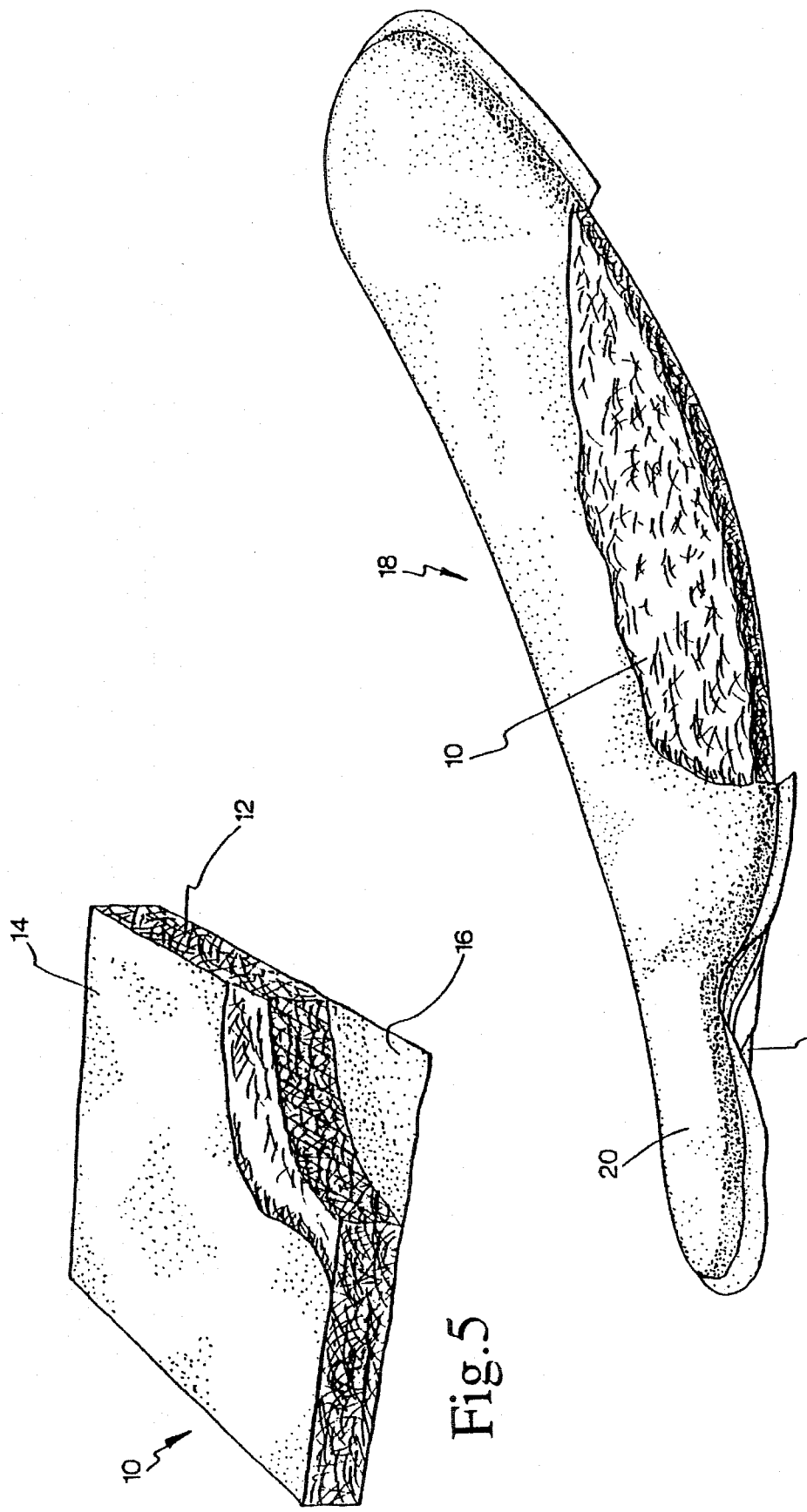

SPHAGNUM MOSS COMPOSITION FOR THE PRODUCTION OF SHEETED ABSORBENT AND METHOD FOR EVALUATING THE POTENTIAL OF SPHAGNUM MOSS MATERIAL FOR ABSORBING LIQUID

FIELD OF THE INVENTION

The invention relates to a novel sphagnum moss composition for the production of a liquid-absorbent medium suitable for use in disposable absorbent articles such as sanitary napkins, tampons, diapers, adult briefs, urinary pads, wound dressings and the like. The novel composition comprises primarily sphagnum moss species selected from the botanical sections of PALUSTRIA, ACUTIFOLIA, RIGIDA, CUSPIDATA, SUBSECUNDA and combinations thereof. The invention also extends to a novel method for evaluating the capacity of sphagnum moss material to absorb liquid, to a method for selectively harvesting raw sphagnum moss and to a novel method for manufacturing an unusually absorbent, structurally integral product containing sphagnum moss material.

BACKGROUND OF THE INVENTION

The prior art has recognized the potential of sphagnum moss material for use as an absorbent medium in structures for absorbing body exudate. Sphagnum moss has highly desirable liquid-absorption properties such as a remarkable absorption capacity and the ability of desorbing adjacent materials by continuing to pull or wick liquid away from them over a long time period such that virtually all the liquid is collected in the sphagnum moss core. These attributes allow the material to provide highly efficient absorbent components which can be made relatively thin for better fit, comfort and discretion, while being sufficiently absorbent to prevent overflow leakage and garment staining.

The following United States patents document the use of sphagnum moss material for manufacturing absorbent components for disposable absorbent products:

| U.S. Pat. No. | INVENTOR | DATE ISSUED |
| --- | --- | --- |
| 4,170,515 | Lalancette et al. | Oct. 9, 1979 |
| 4,215,692 | Levesque | Aug. 5, 1980 |
| 4,226,237 | Levesque | Oct. 7, 1980 |
| 4,305,393 | Nguyen | Dec. 15, 1981 |
| 4,473,440 | Ovans | Sept. 25, 1984 |
| 4,507,122 | Levesque | March 26, 1985 |
| 4,618,496 | Brasseur | Oct. 21, 1986 |
| 4,676,871 | Cadieux et al. | June 30, 1987 |
| 4,992,324 | Dubé | Feb. 12, 1991 |
| 5,053,029 | Yang | Oct. 1, 1991 |

The subject matter of these patents is incorporated herein by reference.

Sphagnum moss material for use in manufacturing absorbent components is harvested from a sphagnous bog and transported to the processing site where it is refined and converted into a structurally integral continuous sheet. In sheet form, the sphagnum moss material can be conveniently rolled up for storage and transportation and it is suitable for direct processing in the high speed automatic equipment that is currently used by the industry for assembling multi-layer disposable absorbent products.

Broadly stated, the process for converting raw sphagnum moss into a structurally integral continuous sheet begins with forming the raw material into an aqueous slurry that is wet classified to extract from the particle suspension the extremely fine particles, commonly referred to as fines, and large pieces of material including roots, branches and the like that do not significantly contribute to the absorbency of the final product. The refined slurry is sheeted on a Fourdrinier wire, dewatered and dried. The resulting structurally integral sheet is calendered to diminish the average pore size of the network in order to increase its drying power.

The prior art also suggests to employ additives for improving certain characteristics of the structurally integral sheet. In particular, the sphagnum moss can be treated with wetting agent in order to develop a superior affinity for aqueous liquids. Polyester fibers can be integrated into the sphagnum moss matrix to increase its resistance. These examples illustrate the variety of possible treatments that have a common objective to improve the liquid-absorption and the mechanical properties of the structurally integral sheet.

One area of the structurally integral sheet that has not yet been explored for the purpose of further improving its liquid-absorption properties is the composition of the sphagnum moss material. A better understanding of the relationship between absorbency and the composition of this vegetal absorbent medium is highly desirable to enable the manufacture of sanitary products having largely improved absorbent properties.

OBJECTIVES AND SUMMARY OF THE INVENTION

An object of the present invention is to provide a liquid-absorbing material containing primarily sphagnum moss of controlled composition, that has enhanced liquid-absorption properties.

Another object of the invention is a method to evaluate the liquid-absorption properties of sphagnum moss material, particularly of a naturally occurring raw sphagnum moss aggregate to determine if it constitutes a suitable starting material for manufacturing a highly absorbent, structurally integral sheet.

A further object of the invention is a method for selectively harvesting sphagnum moss from a sphagnous bog in order to gather raw material that is the most suitable for manufacturing highly absorbent structures.

Yet, another object of the invention is a novel method for manufacturing a structurally integral product containing sphagnum moss material, that has enhanced liquid-absorption properties.

The generic expression "sphagnum moss" designates a vast range of botanical species that co-exist in random proportions in a sphagnous bog. The present inventors have made the unexpected discovery that when sphagnum moss is harvested from a stratum of the bog in which the plants are mainly undecomposed, i.e. having a Von Post value in the range from about 1 to about 3 on a scale of 10, the composition of the sphagnum moss greatly influences the liquid-absorbtion behaviour of the absorbent product.

As embodied and broadly described herein, the invention provides a structurally integral liquid-absorbent product containing primarily substantially undecomposed particles of sphagnum moss plants that belong to at least two botanical sections selected from the group consisting of PALUSTRIA, ACUTIFOLIA, RIGIDA, SUBSECUNDA and CUS- PIDATA, said structurally integral liquid-absorbent product having an absorbency performance index in the range from about 1 to less than 4. Preferably, the performance index is in the range from about 2 to less than 4 and most preferably in the range from about 3 to less than 4.

The absorbency performance index is established on the basis of two factors. The first is the identity of the sphagnum moss species present in the absorbent product and the second the proportions of the species in the composition.

A wide variety of sphagnum moss species exist in nature. According to taxonomy rules the individual sphagnum moss species are classified in sections according to common traits. The primary sections that are considered for calculating the absorbency performance index are PALUSTRIA, ACUTIFOLIA, RIGIDA, SUBSECUNDA and CUSPIDATA. These five sections which are the most prevalent in the North American continent are given the following rating on a judgemental base of observed liquid-absorption performance.

| SECTION | RATING |
| --- | --- |
| PALUSTRIA | 4 |
| ACUTIFOLIA | 3 |
| RIGIDA | 2 |
| SUBSECUNDA | 2 |
| CUSPIDATA | 1 |

A species that belongs to any other section is assigned a rating of zero (0) points, i.e. that species does not contribute to elevate the absorbency performance index in any way, as it will be described hereinafter.

The absorbency performance index is the weighted average of the ratings of the various botanical sections present in the sphagnum moss aggregate. This step is best illustrated by an example. A sphagnum moss aggregate having the following composition:

| SECTION | PERCENTAGE OF ONE OR MORE SPECIES IN THE SPHAGNUM MOSS AGGREGATE THAT BELONG TO A COMMON SECTION |
| --- | --- |
| PALUSTRIA | 60.3 |
| ACUTIFOLIA | 31.7 |
| CUSPIDATA | 4.1 |
| RIGIDA | 1.7 |
| SUBSECUNDA | 1.5 |
| SQUARROSA | 0.1 | provides the following performance index:

| | |
| --- | --- |
| (4 × 0.603) | Palustria |
| + (3 × 0.317) | Acutifolia |
| + (1 × 0.041) | Cuspidata |
| + (3 × 0.017) | Rigida |
| + (2 × 0.015) | Subsecunda |
| + (0 × 0.001) | Squarrosa |
| 3.488 | |

It should be noted that the performance index calculation takes into account only the species of sphagnum moss and no consideration is given to other constituents that could be intermixed with the sphagnum moss. For example, the performance index of a structurally integral sheet of sphagnum moss containing a proportion of other material, such as Kraft wood pulp or polyester fibers, is established solely on the basis of the characteristics of the sphagnum moss constituent and the presence of Kraft wood pulp fibers has no bearing on the calculated performance index value.

A rating of zero (0) points with regard to a certain sphagnum moss species is not intended to mean that the species has necessarily little or no ability to take-up liquid. A zero rating is used solely to withdraw the contribution of a certain species to build-up the performance index either because the species truly is not absorptive or because its performance is unknown. It should be appreciated that the performance index has a valid significance only when the sphagnum moss contains primarily one or more species selected from the botanical sections of PALUSTRIA, ACUTIFOLIA, RIGIDA, SUBSECUNDA CUSPIDATA and mixtures thereof. Small amounts of one or more species in the composition that belong to a different section do not significantly affect the accuracy of the performance index. However, if a species from a section other than PALUSTRIA, ACUTIFOLIA, RIGIDA, SUBSECUNDA or CUSPIDATA predominates, the performance index is no longer a valid indicator of the liquid-absorbency potential of the sphagnum moss.

As embodied and broadly described herein, the invention also provides a disposable absorbent product, comprising:

an absorbent core including primarily substantially undecomposed particles of sphagnum moss plants that belong to at least two botanical sections selected from the group consisting of PALUSTRIA, ACUTIFOLIA, RIGIDA, SUBSECUNDA and CUSPIDATA, said absorbent core having an absorbency performance index in the range from about 1 to less than 4; and a body contacting, liquid-pervious layer superposed to said absorbent core.

In a preferred embodiment, the disposable absorbent product is a sanitary napkin, a diaper, an adult incontinence brief, a urinary pad or a wound dressing and further includes a liquid-impervious layer underneath the absorbent core to prevent body exudate from egressing the disposable absorbent product from its garment facing surface. Most preferably, the liquid-pervious and the liquid-impervious layers are bonded to one another to form a jacket in which the absorbent core is held captive.

The rating system established to calculate the performance index suggests that sphagnum moss constituted entirely of one or more species belonging to the PALUSTRIA section would have excellent liquid absorbency characteristics. However, raw sphagnum moss having such an ideal composition is rarely encountered in nature. Rather, aggregates of species from various sections are predominant. Since the composition of such aggregates can widely vary to include species that are not particularly desirable from the stand point of liquid-absorbency, the absorbent properties of sheets made from this material are likely to vary in accordance with the specific composition of the raw material.

From this perspective, the invention can be defined in broad terms as a structurally integral absorbent product containing primarily a composition of substantially undecomposed sphagnum moss, said composition having a major fraction constituted by at least one species that belongs to the botanical section PALUSTRIA and a smaller fraction including one or more sphagnum moss species selected from the botanical sections group consisting of ACUTIFOLIA, RIGIDA, SUBSECUNDA and CUSPIDATA.

The invention also provides a method for manufacturing a highly absorbent, structurally integral sheet. The method comprises the steps of:

providing a starting material containing particles of sphagnum moss plants that belong to at least two botanical sections selected from the group consisting of PALUSTRIA, ACUTIFOLIA, RIGIDA, SUBSECUNDA and CUSPIDATA, said sphagnum moss having a Von Post value in the range from about 1 to about 3, said starting material having a performance index in the range from about 1 to less than 4; and forming said starting material into a structurally integral sheet.

The present invention also provides a method for evaluating the liquid-absorbency of a material containing primarily substantially undecomposed sphagnum moss plants (herein "plant" designates a vegetal organism in its entirety or a fraction of that organism such as a leaf or a fragment of a leaf) selected from the group of botanical sections consisting of PALUSTRIA, ACUTIFOLIA, RIGIDA, SUBSECUNDA, CUSPIDATA and mixtures thereof. This method is particularly useful to determine whether a naturally occurring raw sphagnum moss composition is a suitable starting material for manufacturing a highly absorbent structurally integral sheet. Broadly stated, the method comprises the following steps:

A) sorting said sphagnum moss plants into predetermined classes on the basis of liquid-absorption properties of said sphagnum moss plants, whereby one class contains sphagnum moss plants more desirable in terms of liquid-absorption than sphagnum moss plants assigned to another class;

B) determining the proportions of said predetermined classes with respect to amount of sphagnum moss plants per class; and C) calculating a mean of the proportions determined at step B adjusted to account for different liquid-absorbency characteristics of sphagnum moss plants belonging to different classes, said mean being indicative of an ability of said material to absorb liquid.

The allocation of the sphagnum moss plants in classes allows to rank the plants in terms of ability to absorb liquid. Accordingly, sphagnum moss plants that belong to a common class exhibit identical or similar liquid absorption properties. In a preferred embodiment, the classification of the sphagnum moss plants is established according to visually observable morphological relationships. Since the liquid-absorbency attributes of a sphagnum moss plant are dependent upon its form and structure, morphological similarity between plants entails common liquid-absorbency properties. This approach has a practical advantage in that a simple microscopic examination of the sphagnum moss is usually sufficient to complete the classification procedure, with no necessity to perform complicated and time consuming tests.

In a most preferred embodiment the classes of sphagnum moss plants correspond to botanical sections. For instance, the classification consists of conducting a microscopic examination of the sphagnum moss composition in order to identify the botanical species present in the sample. A visual count is performed in order to determine approximately the proportions of the species identified in the sphagnum moss composition. The results for species that belong to a common botanical section are added up in order to express the proportions per botanical sections.

The botanical sections are ranked in terms of ability to absorb liquid by using the same system developed for the calculation of the performance index discussed above. More particularly, a parameter is associated to each section whose value provides a relative measure of the liquid-absorbency of the section and a weighted average of the various parameter values is calculated to obtain a measure of the absorbency of the sphagnum moss composition.

As embodied and broadly described herein, the invention further provides a method for selectively harvesting vegetable raw material from a sphagnum moss growing site for use in manufacturing liquid-absorbent structures, said growing site containing an aggregate of sphagnum moss species that predominantly belong to a group of botanical sections consisting of PALUSTRIA, ACUTIFOLIA, RIGIDA, SUBSECUNDA and CUSPIDATA, a composition of said aggregate varying randomly over said growing site, whereby vegetable raw material harvested at different locations on said growing site has non-uniform liquid-absorbent properties, said method comprising the steps of:

identifying an area of said growing site on which is present sphagnum moss aggregate having a composition that meets a predetermined criterion, said criterion having reference to an ability of said sphagnum moss aggregate to absorb liquid; and harvesting vegetable raw material having a Von Post in the range from about 1 to about 3 from said area.

This method allows an efficient exploitation of the biomass present in a sphagnous bog where the sphagnum moss species are present in an erratic fashion. By sampling the bog and evaluating the liquid-absorbency potential of the raw sphagnum moss at various locations, a representation of the bog can be drawn to indicate the areas where the most desirable sphagnum moss is located.

As embodied and broadly described herein, the invention further provides a method for manufacturing a structurally integral liquid-absorbent product from vegetable raw material harvested from a sphagnum moss growing site, said growing site containing an aggregate of sphagnum moss species that predominantly belong to a group of botanical sections consisting of PALUSTRIA, ACUTIFOLIA, RIGIDA, SUBSECUNDA and CUSPIDATA, a composition of said aggregate varying randomly over said growing site, whereby vegetable raw material harvested at different locations on said growing site has non-uniform liquid-absorbent properties, said method comprising the steps of:

identifying an area of said growing site on which is present sphagnum moss aggregate having a composition that meets a predetermined criterion, said criterion having reference to an ability of said sphagnum moss aggregate to absorb liquid;

harvesting vegetable raw material having a Von Post in the range from about 1 to about 3 from said area; and forming the vegetable raw material harvested from said area into a structurally integral, liquid-absorbent product.

As embodied and broadly described herein, the invention also provides a structurally integral liquid-absorbent product containing primarily substantially undecomposed particles of sphagnum moss plants that belong to at least one species selected from the group consisting of:

1) all species from the botanical section ACUTIFOLIA;

2) all species from the botanical section RIGIDA;

3) all species from the botanical section SUBSECUNDA;

4) all species from the botanical section CUSPIDATA;

5) *Sphagnum centrale, Sphagnum erythrocalyx, Sphagnum henryense, Sphagnum perichaetiale, Sphagnum portoricence* from the botanical section PALUSTRIA, said structurally integral liquid-absorbent product having an absorbency performance index in the range from about 1 to about 4.

BRIEF DESCRIPTION OF THE DRAWINGS

The file of this application contains at least one drawing executed in color. Copies of this patent with color drawings will be provided by the Patent and Trademark Office upon request and payment of the necessary fee.

FIG. 5 is a fragmentary perspective view of a structurally integral sphagnum moss sheet in accordance with the invention; and FIG. 6 is a fragmentary perspective view of a sanitary napkin in accordance with the invention.

DESCRIPTION OF A PREFERRED EMBODIMENT

Sphagnum moss is a plant which grows from the top while the bottom part of the plant dies and gradually decomposes into peat. As it is well known, sphagnous bogs, commonly referred to as peat bogs, typically have a vertical cross-sectional stratification. The top most layer of the bog is comprised of leaves, branches and flowers of living flora, predominantly the living sphagnum moss plant but also including other-plants growing on the bog. The top most layer extends to a depth in the range from about 2.5 centimeters to about 18 centimeters.

Below the topmost layer is a first intermediate layer consisting of undecomposed dead sphagnum moss including the roots of other living plants. The first intermediate layer is characterized by being fibrous, relatively light coloured, with the plant structure generally intact. Such a layer may extend from a depth in the range from about 18 centimeters to about 1 meter below the surface.

Below the first intermediate layer is located a second intermediate layer of partially decomposed sphagnum moss which can generally be distinguished from the first intermediate layer by a clear line of colour demarcation. The second intermediate layer is characterized by increasingly darkening colour and increasing plant structure degradation as the depth increases, to a point where the plant structure is no longer apparent and it shades from brown to black. The lower portion of the second intermediate layer is typically a portion of the sphagnous bog utilized as fuel. This layer may extend from a depth in the range from about 1 meter to about 2.5 meters from the surface.

Below the second intermediate layer is the bottom layer which is the last stage of decomposition of the sphagnum moss plant. The bottom layer is commonly referred to as "black earth" and is characterized by having essentially no discernable plant structure and a black colour. This material may be found at a depth in the range from about 2.5 meters to about 4 meters from the surface. In some instances, sphagnous bogs do not comprise this layer.

Figure 1:
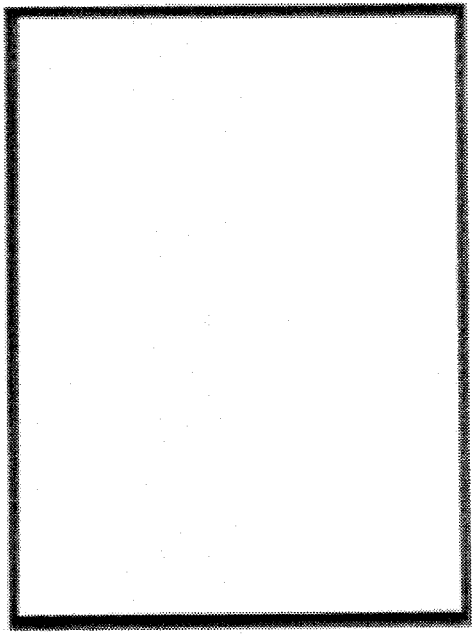
FIGS. 1 to 4 are colour samples provided as reference for determining the Von Post value of sphagnum moss material.
Figure 2:
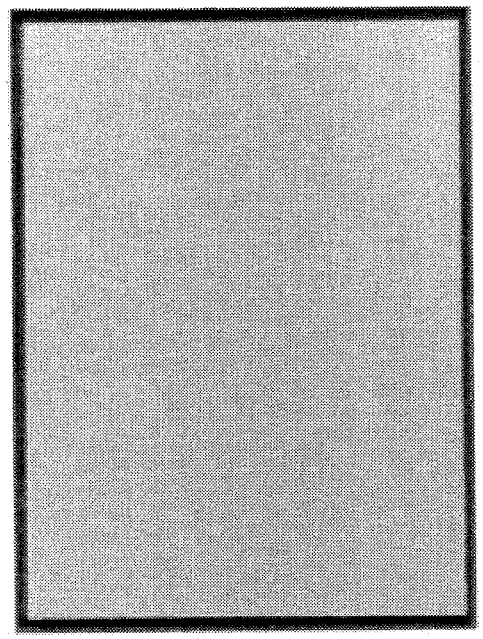
Figure 3:
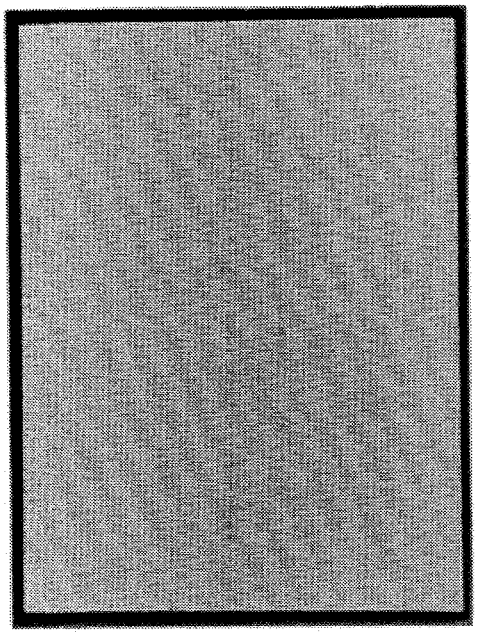
Figure 4:
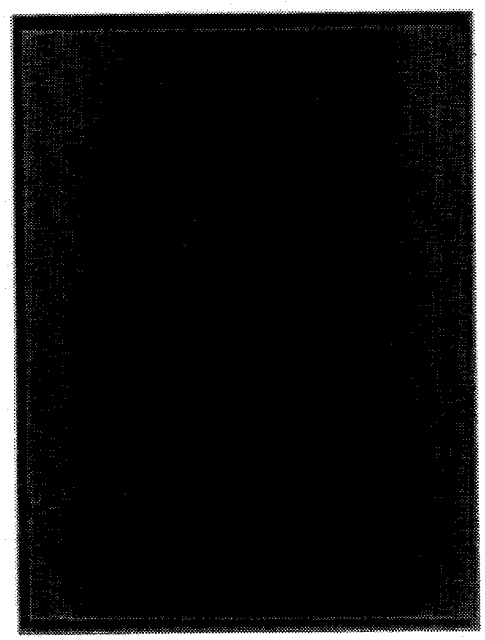

The Von Post method is an effective tool to characterize the degree of decomposition of dead sphagnum moss. The test consists of pressing samples of sphagnum moss gathered at different depths and comparing the expelled water with the colour chart provided in FIGS. 1, 2, 3 and 4. A value 1 is assigned to sphagnum moss from the layer of the bog which releases a clear liquid having a colour matching FIG. 1. A value 2 is assigned to sphagnum moss located somewhat deeper and showing some degree of decomposition. The water that is being released is lightly coloured as shown in FIG. 2. Von Post values from 3 to 10 are assigned to sphagnum moss gathered at an increasing depth and showing increasing degree of decomposition so that the expelled water becomes progressively darker and holds more and more organic particles. FIGS. 3 and 4 show the colour of water expelled from samples having a Von Post value of 3 and 4, respectively. Colour charts for Von Post values beyond 4 have not been provided because they are not deemed necessary for the purpose of understanding the present invention.

The number of sphagnum species present in North America is considerable. The following list provides the sphagnum species found north of Mexico:

A. Section PALUSTRIA
* Sphagnum centrale
Sphagnum erythrocalyx
Sphagnum henryense
* Sphagnum imbricatum
* Sphagnum magellanicum
* Sphagnum palustre
* Sphagnum papillosum
Sphagnum perichaetiale
Sphagnum portoricence B. Section RIGIDA
Sphagnum compactum
Sphagnum strictum C. Section SQUARROSA
* Sphagnum squarrosum
* Sphagnum teres D. Section INSULOSA
* Sphagnum aongstroemii E. Section SUBSECUNDA
* Sphagnum auriculatum
Sphagnum carolinianum
* Sphagnum contortum
Sphagnum crispum
Sphagnum cyclophyllum
* Sphagnum inundatum
Sphagnum orientale
* Sphagnum platyplyllum
Sphagnum perfoliatum
Sphagnum pylaesii
Sphagnum subobesum
Sphagnum subsecumdum F. Section ISOCLADUS
Sphagnum macrophyllum
Section CUSPIDATA
* Sphagnum angustifolium
  Syn: S. parvifolium
  S. recurvum var. tenue
* Sphagnum annulatum
* Sphagnum annulatum var porosum
  Syn: S. jensenii
* Sphagnum balticurn
* Sphagnum cuspidatum
* Sphagnum fallax
  Syn: S. apiculatum
  S. recurvum var. mucronatum
Sphagnum fitzgeraldii
Sphagnum flexuosum
  Syn: S. amblyphyllum
  S. recurvum var amblyphyllum
* Sphagnum lenense
* Sphagnum lindbergii
* Sphagnum majus
  Syn: S. dusenii
Sphagnum mendocium
* Sphagnum obtusum
* Sphagnum pulchrum

* *Sphagnum riparium*
* *Sphagnum splendens*
* *Sphagnum tenellum*
* *Sphagnum torreyanum*

H. Section POLYCLADA
* *Sphagnum wulfianum*

I. Section ACUTIFOLIA
* *Sphagnum andersonianum*
* *Sphagnum angermanicum*
  *Sphagnum bartlettianum*
* *Sphagnum fimbriatum*
* *Sphagnum flavicomans*
* *Sphagnum fuscum*
* *Sphagnum girgensohnii*
  *Sphagnum junghuhnianum*
  *Sphagnum meridense*
* *Sphagnum nemoreum*
    Syn: *S. capillaceum*
    *S. acutifolium*
    *S. Capillifolium*
* *Sphagnum quinquefarium*
* *Sphagnum rubellum*
* *Sphagnum russowii*
    Syn: *S. Robustum*
* *Sphagnum subfulvum*
  *Sphagnum subnitens*
    Syn: *S. plumulosum*
  *Sphagnum subtile*
  *Sphagnum tenerum*
* *Sphagnum warnstorfii*
    Syn: *S. warnstorfianum*

An evaluation of the absorbent properties of individual sphagnum species from various sections has lead to the unexpected finding that the absorbent properties vary substantially from one section to another. This finding has been made by studying the following pure living species of sphagnum moss:

| SPECIES | SECTIONS |
| --- | --- |
| Fuscum | ACUTIFOLIA |
| Rubellum | ACUTIFOLIA |
| Magellanicum | PALUSTRIA |
| Papillosum | PALUSTRIA |
| Recurvum | CUSPIDATA |
| Cuspidatum | CUSPIDATA |
| Subsecundum | SUBSECUNDA |
| Compactum | RIGIDA |

The evaluation of the liquid-absorbency of those species is made by forming the pure sphagnum species into structurally integral sheets on which tests are performed. A structurally integral sheet is formed by first converting raw sphagnum moss of a given species into a slurry. This is accomplished by treating the sphagnum moss in a standard 0.45 kilogram (kg) Valley Beater with a load of 1 kg for a period of 5 minutes (min). At the end of the treatment a solution of di-octyl sufosuccinate (0.1% by weight of the total suspension) is added to the slurry. The di-octyl sufosuccinate solution is a rewetting agent commercially available under the brand name "Alcopol 60" from the Allied Colloids Company.

The slurry is then laid on a square foraminous plate of 30.5 centimeters (cm) by 30.5 cm and dried at 150° C. to a bone dry condition. The sheet is then re-humidified in a standard Tenney Cabinet maintained at 65% relative humidity. The sheet is maintained in the Tenney Cabinet until it has regained 20% w/w of water vapour.

For some of the liquid-absorbency tests the sheet is calendared between a pair of rolls having a diameter of 20.3 cm at a pressure of approximately 550 kg per linear cm.

The sample sheets of each sphagnum moss species is subjected to the tests B to G described hereinafter. Test A is an exception because it uses as sample material a slurry of sphagnum moss, not the structurally integral sheets employed for the other tests.

A. RETENTION PROFILE OF THE NEVER DRIED PASTE UNDER VARIOUS LOADS OF 0 grams per square centimeter (g/cm$^2$), 17.6 g/cm$^2$ and 105.50 g/cm$^2$ A slurry of sphagnum moss material is fully saturated and placed into a cylindrical container having a perforated bottom wall. Uniform pressure is exerted on the sphagnum moss and the amount of water expelled at 0 g/cm$^2$, 17.6 g/cm$^2$ and 105.5 g/cm$^2$ pressure is recorded in order to calculate the amount of water retained per gram of dry sphagnum moss at those pressures. The results are expressed in the following table.

| SPECIES | RETENTION AT 0 g/cm$^2$ pressure (cc/g) | RETENTION AT 17.6 g/cm$^2$ pressure (cc/g) | RETENTION AT 105.5 g/cm$^2$ pressure (cc/g) |
| --- | --- | --- | --- |
| Fuscum | 38 | 27 | 17 |
| Rubellum | 36 | 24 | 16 |
| Magellanicum | 53 | 32 | 21 |
| Papillosum | 51 | 33 | 18 |
| Recurvum | 38 | 27 | 17 |
| Cuspidatum | 47 | 27 | 16 |
| Subsecundum | 44 | 38 | 17 |
| Compactum | 41 | 37 | 16 |

B. SATURATION CAPACITY (Gravimetric Absorbency Test System) UNDER A LOAD OF 7.04 g/cm$^2$ ON THE NON-CALENDERED SHEET The gravimetric absorbency test system (hereinafter "GATS") is utilised to measure the ultimate absorbent capacity of a porous network. The GATS instrument comprises a horizontal porous plate made of fritted glass in fluid communication with a vertical burette filled with an aqueous solution. The test procedure consists of placing the non-calendared sample sheet in contact with the fritted glass plate under a pressure of 7.04 g/cm$^2$ for allowing the sample sheet to absorb the aqueous solution under the effect of capillary attraction. The aqueous solution is supplied at the interface between the fritted glass plate and the sample material under a negative pressure head of one centimeter which is achieved by maintaining the level of aqueous solution in the burette one centimeter below the top surface of the fritted glass plate. To prevent an undesirable pressure head increase due to the absorption of aqueous solution from the fritted glass plate an electro-mechanical control system replenishes the burette at the same rate as the aqueous solution is withdrawn therefrom to maintain the level of aqueous solution constant.

The absorption of aqueous solution will cease when the residual capillary attraction of the sample material is counterbalanced by the negative pressure head. The amount of aqueous solution extracted from the burette is then observed and it is divided by the weight of the sample to obtain the maximal absorbent capacity of the sample material per unit of weight. The results of this test are reported in the Table below.

| SPECIES | GATS results (cc/g) |
| --- | --- |
| Fuscum | 24.5 |
| Rubellum | 22.0 |
| Magellanicum | 18.0 |
| Papillosum | 20.0 |
| Recurvum | 23.5 |
| Cuspidatum | 21.5 |
| Subsecundum | 26.0 |
| Compactum | 23.0 |

C. SATURATION CAPACITY (Gravimetric Absorbency Test System) UNDER A LOAD OF 7.04 g/cm² ON THE CALENDERED SHEET, BOTH WITH A CYCLE OF 7.04 g/cm² THEN 35.19 g/cm² THEN 7.04 g/cm²

The same procedure set forth in B above is followed with the following exception. When the absorption of aqueous solution by the sample under a pressure of 7.04 g/cm² has ceased, the pressure is increased to 35.19 g/cm² and the amount of aqueous solution remaining in the sample is noted. The pressure is released to 7.04 g/cm² and the amount of liquid in the sample observed again. The results of this test are reported in the following Table.

| SPECIES | GATS AT 7.04 g/cm² | GATS AT 35.19 g/cm² | GATS AT 7.04 g/cm² |
| --- | --- | --- | --- |
| Fuscum | 17.1 | 11.9 | 15.7 |
| Rubellum | 16.7 | 10.4 | 16.3 |
| Magellanicum | 24.1 | 14.3 | 22.0 |
| Papillosum | 22.2 | 12.4 | 19.7 |
| Recurvum | 16.7 | 9.7 | 15.1 |
| Cuspidatum | 18.4 | 10.8 | 16.4 |
| Subsecundum | 20.0 | 10.7 | 17.1 |
| Compactum | 20.8 | 10.8 | 18.5 |

D. WICKING AT 45° ANGLE (CAPACITY AND HEIGHT) OF THE CALENDARED SHEET

The sample material is inclined at 45° and its lower edge immersed in a pool of aqueous solution. As a result of capillary attraction liquid is absorbed by the sample and travels longitudinally against gravity. The distance in centimeters travelled by the liquid front measured from the lower edge of the sample is recorded at 15 min, 30 min, 60 min and 120 min. At those time intervals the amount of liquid within the sample is also recorded. This measurement is made by weighing the sample and subtracting from the measure the weight of the dry sample. The amount of liquid absorbed by the sample is normalized on the basis of a dry sample having a basis weight of 100 g/m² and having a width of 1 cm. The results of this test are reported in the following Tables.

| SPECIES | Position of liquid front at 15 min (cm) | Position of liquid front at 30 min (cm) | Position of liquid front at 60 min (cm) | Position of liquid front at 120 min (cm) |
| --- | --- | --- | --- | --- |
| Fuscum | 14 | 17 | 23 | 26 |
| Rubellum | 14 | 17 | 22 | 26 |
| Magellanicum | 13 | 14 | 23 | 27 |
| Papillosum | 14 | 17 | 22 | 26 |
| Recurvum | 11 | 12 | 15 | 16 |
| Cuspidatum | 9 | 14 | 17 | 22 |
| Subsecundum | 11 | 12 | 14 | 16 |
| Compactum | 13 | 15 | 17 | 21 |

| SPECIES | Amount of liquid picked-up at 15 min | Amount of liquid picked-up at 30 min | Amount of liquid picked-up at 60 min | Amount of liquid picked-up at 120 min |
| --- | --- | --- | --- | --- |
| Fuscum | 1.4 | 1.6 | 2.0 | 2.3 |
| Rubellum | 1.3 | 1.6 | 1.8 | 2.2 |
| Magellanicum | 1.4 | 1.8 | 2.3 | 2.6 |
| Papillosum | 1.6 | 2.0 | 2.4 | 2.8 |
| Recurvum | 1.1 | 1.3 | 1.4 | 1.6 |
| Cuspidatum | 0.9 | 1.1 | 1.5 | 1.8 |
| Subsecundum | 1.1 | 1.2 | 1.4 | 1.6 |
| Compactum | 1.4 | 1.6 | 1.8 | 2.2 |

E. CAPACITY OF LIQUID IMPACT AT 45° ANGLE OF THE CALENDARED SHEET

The impact capacity is measured by weighing the amount of fluid that is retained in a sample of 10.16 cm by 17.78 cm placed on a 45° inclined plane, on which is released an amount of aqueous solution corresponding to ten times the weight of the sample, from an overhanging burette. The burette barely touches the sample at a point approximately 1.2 cm away from its upper extremity. The amount of liquid retained by the sample is expressed in terms of percentage of the total amount of liquid released. The results of this test are reported in the following Table.

| SPECIES | 45° impact capacity (%) |
| --- | --- |
| Fuscum | 100 |
| Rubellum | 88 |
| Magellanicum | 93 |
| Papillosum | 99 |
| Recurvum | 43 |
| Cuspidatum | 76 |
| Subsecundum | 10 |
| Compactum | 99 |

F. DRYING POWER OF THE CALENDARED SHEET

A sample of sphagnum material sheet having a size of 5.08 cm by 25.4 cm is provided. A test pad of pulp fluff material having a basis weight of 200 g/m² and wetted with an amount of aqueous solution corresponding to 5 cubic centimeters per gram of the sphagnous sample is deposited on the sphagnous sample. The amount of liquid drawn by the sample is measured at 30 min, 120 min and 180 min. The measurement is made by weighing the test pad and subtracting from the measurement the weight of the dry pad. The results are expressed by dividing the weight of the liquid remaining in the test pad by the weight of the dry test pad.

The result of this test are reported in the following table.

| SPECIES | Amount of liquid in test pad at 30 min | Amount of liquid in test pad at 120 min | Amount of liquid in test pad at 180 min |
|---|---|---|---|
| Fuscum | 5.8 | 3.1 | 2.7 |
| Rubellum | 6.9 | 3.5 | 2.8 |
| Magellanicum | 5.3 | 2.5 | 2.15 |
| Papillosum | 5.80 | 2.7 | 2.25 |
| Recurvum | 9.5 | 8.2 | 8.0 |
| Cuspidatum | 5.1 | 3.2 | 2.8 |
| Subsecundum | 10.2 | 8.8 | 8.4 |
| Compactum | 9.3 | 7.4 | 6.4 |

G. POROUS PLATE RETENTION AT −40 cm HYDROSTATIC

The sample of sphagnum material is fully saturated and placed on a perforated plate that sits on one leg of a U-shaped tube. The level of water in the tube is maintained 40 cm below the sample, whereby a negative hydrostatic pressure corresponding to 40 cm is maintained constant against the sample. The amount of water retained in the sample is observed and expressed in terms of weight of the dry sample. The results of this test are reported in Table 6.

| SPECIES | Retention - 40 cm hydrostatic |
|---|---|
| Fuscum | — |
| Rubellum | — |
| Magellanicum | 8.0 |
| Papillosum | 6.5 |
| Recurvum | 4.5 |
| Cuspidatum | 5.0 |
| Subsecundum | 4.5 |
| Compactum | 5.5 |

The test results are compiled and the sphagnum moss species are ranked in terms of the three best performers in each test category. The results are shown in the following table.

RESULTS OF ABSORBENCY TESTS FOR VARIOUS SPHAGNUM MOSS SPECIES

| TEST A | TEST B | TEST C at 7.04 g/cm² | TEST C at 35.19 g/cm² | TEST D wicking height | TEST D capacity | TEST E | TEST F | TEST G |
|---|---|---|---|---|---|---|---|---|
| Magell. | Compac. | Magell. | Magell. | Magell. | Papill. | Fuscum | — | Magell. |
| Papill. | Subsec. | Papill. | Papill. | Papill. | Magell. | Papill. | Cuspid. | — |
| Cuspid. | Recurv. | Compact. | Fuscum | Fuscum | Fuscum | Compact. | Magell. | Papill. |

The species are then ranked by frequency of appearance as follows.

| SPECIES | FREQUENCY OF APPEARANCE | SECTION |
|---|---|---|
| Fuscum | 4 | ACUTIFOLIA |
| Rubellum | 0 | ACUTIFOLIA |
| Magellanicum | 7 | PALUSTRIA |
| Papillosum | 7 | PALUSTRIA |
| Recurvum | 1 | CUSPIDATA |
| Cuspidatum | 2 | CUSPIDATA |
| Subsecundum | 1 | SUBSECUNDA |
| Compactum | 3 | RIGIDA |

The absorbency characteristics of sphagnum moss are determined by the plant structure, such as the relative size of the leaves and their quantity, among others. Accordingly, it is theorized that the morphological resemblance between all species of a given section entails that the species of the section will share common liquid-absorbency characteristics. On the basis of this principle, the variability in the liquid-absorbency characteristics observed between different sphagnum moss species can be reduced to variability between sections. Consequently, the results of the tests A to F can now be expressed in terms of frequency of appearance of each section in the top three ranks of each test. This is achieved by summing, for each section, the frequencies of appearance of its species. The results are expresses below:

| SECTION | FREQUENCY OF APPEARANCE |
|---|---|
| PALUSTRIA | 14 |
| ACUTIFOLIA | 4 |
| CUSPIDATA | 3 |
| RIGIDA | 3 |
| SUBSECUNDA | 1 |

Finally, the sections are assigned the following performance rating based on frequency of appearance:

| SECTION | RATING |
|---|---|
| PALUSTRIA | 4 |
| ACUTIFOLIA | 3 |
| CUSPIDATA | 2 |
| RIGIDA | 2 |
| SUBSECUNDA | 1 |

It is important to note that the observed relationship between plant origin and liquid-absorbency is verified only if the sphagnum moss is dead and mainly undecomposed, i.e. having a Von Post value in the range from about 1 to about 3, most preferably in the range from about 1 to about 2. A Von Post value significantly higher than 3 indicates a highly decomposed plant that has lost its morphological identity. Consequently, the liquid-absorbency of the decomposed plant is no longer correlated to its structure.

In situations where the sphagnum moss is a composition, comprising species from different sections, the quality of the composition as liquid-absorbent medium can be estimated by calculating the performance index which is the average weighted absorbency rating. This is achieved by summing up the respective performance ratings assigned to the different sections present in the sphagnum moss composition, multiplied by the respective proportions of the various sections. For example, in a sphagnum moss composition comprising 65% of sphagnum moss species from the PALUSTRIA section and 35% by weight of sphagnum moss species from the ACUTIFOLIA section, the average weighted absorbency rating is (4×0.65)+(3×0.35)=3.65.

The calculation of the performance index takes in consideration only the sphagnum moss constituents of the composition and no regard is given to other kinds of ingredients. For example it is common to incorporate in sphagnum moss absorbent cores polyester fibers in order to increase the structural integrity of the absorbent network. In such sphagnum moss composition, the fibrous polyester ingredient in transparent to the calculation of the performance index. Secondly, the performance index is a valid indicator of the ability of a certain composition to absorb liquid only when the composition comprises a significant proportion of sphagnum moss selected from the sections group constituted by PALUSTRIA, ACUTIFOLIA, RIGIDA, SUBSECUNDA, CUSPIDATA and mixtures thereof. If a species from another section is present in minor quantities, it is factored in the performance index calculation by assigning to that section a zero rating which has the effect of neutralising the contribution of the species to build-up the performance index. In reality, the presence of a non-contributing species attenuates the performance index by diminishing the concentration of the recognized and contributing species in the total sphagnum moss fraction.

There are two reasons for assigning a zero rating to a certain section. Firstly, the section may have little or no ability to absorb liquid. Secondly, the section may not have been tested, accordingly its liquid-absorption properties are unknown. In this case, a zero rating allows to complete the calculation of the performance index while maintaining a margin for error, since in most situations the untested species is likely to absorb liquid at least to some degree, therefore the sphagnum moss composition will be somewhat more absorbent than what the performance index suggests.

The ability to evaluate the liquid-absorbency potential of a sphagnum moss composition can be used advantageously to ascertain if a naturally occurring raw sphagnum moss composition is a suitable starting material for manufacturing absorbent cores for disposable absorbent products, that must meet or exceed predetermined liquid-absorbency specifications. Typically, raw sphagnum moss is harvested from a sphagnous bog where various sphagnum moss species are present in an erratic fashion. As a consequence, the composition of the sphagnum moss varies widely from one area of the bog to the other. In order to avoid harvesting raw material from areas of the bog where the composition of the sphagnum moss is not suitable to yield a refined product that is sufficiently absorbent, the sphagnous bog is prospected in order to draw a map of the bog delineating the areas that contain an acceptable sphagnum moss composition from the areas that are susceptible to furnish poorly absorbent raw material. This method allows an efficient exploitation of the biomass by conducting a selective harvesting that produces raw material having consistent liquid-absorbent properties.

The sphagnous bog prospection is carried out by taking samples from different locations and by recording the coordinates of each location. The sampling rate is selected in accordance with the desired resolving power sought from the map. Each sample is then subjected to a microscopic examination in order to identify the species of sphagnum moss that are present and also to estimate the relative count of each species. The visually observed frequency of appearance of each species in the sample is used to establish the proportions of that species in the sphagnum moss composition. The proportions of species that belong to a common section are added together in order to express the composition of the sphagnum moss in terms of sections.

The next step is to calculate the performance index of each sample by assigning to each section present in the sample the proper performance rating and by calculating the weighted performance rating average of the composition. The resulting data is correlated to the coordinates of the sample in order to draw the map of the sphagnous bog that delineates the areas containing sphagnum moss of acceptable composition from the areas of unacceptable material. The map is then used as a guide for selectively harvesting sphagnum moss to obtain raw material of consistent quality.

If it is not desired to map the entire sphagnous bog or large segments thereof, a limited prospection can be performed of a given area immediately before that area is harvested. If the tests indicate the presence of raw material of acceptable quality, the harvesting operation is initiated. However, if the raw material turns out to be unacceptable, the harvesting operation is shifted to another location.

The sphagnum moss harvested from a site of the bog that yields acceptable quality raw material is transported to the processing site for conversion into a structurally integral sheet. The raw sphagnum moss is wet classified to remove the extremely fine material, commonly referred to as fines, and large pieces of material including roots, branches and the like which do not contribute significantly to the absorbency of the peat moss material. The classification is carried out such that anything that remains on a number 10 mesh screen (2000 microns) is discarded and anything that passes through a number 60 mesh screen (250 microns) is also discarded. Preferably, anything that remains on a number 14 mesh screen (1410 microns) is discarded and anything that passes through a number 100 mesh screen (149 microns) is discarded.

The classification is carried out by a wet screening process which consists of forming an aqueous slurry of the raw sphagnum moss material and flowing the slurry through successive screening stages to extract from the slurry the fines and the excessively large particles.

The screened sphagnum moss fraction is diluted with water to a manageable slurry. If desired, a fibrous component may be added to the slurry. The fibrous component may include such materials as Kraft wood pulp and mechanical wood pulp. As used herein, the term mechanical wood pulp is meant to include ground wood pulp, thermo-mechanical pulp and refiner wood pulp. Ground wood is essentially trees and branches which have been debarked, cleaned and then ground into particulate matter. Refiner wood pulp differs from ground wood pulp only in that the grinding step utilizes a refiner, i.e. a disc-like device well known in the art and generally having metallic ribs at the peripheral sections thereof which last contact the wood particles and help separate the wood fibers without excessively damaging them. Thermo-mechanical wood pulp is similar to refiner pulp with the exception that the wood particles are heated when in the refiner, usually with steam, and this heating further aids in separating the wood fibers. The common characteristic of these mechanical pulps is that no attempt has been made to separate the fibers by chemical means although they may later, after being reduced to fine particulate matter, be subjected to a desired chemical treatment.

Preferably, when the mechanical wood pulp is used in the structurally absorbent sheets of this invention such mechanical wood pulp has a Canadian Standard Freeness (TAPPI test method T-227) of from about 60 to 750 and preferably from about 400 to 600.

The Kraft wood pulp, also usable in combination with the peat moss, is essentially chemically treated, long fibered pulp such as sulfite and sulfate wood pulps.

The fibrous component may also include a natural or synthetic textile fiber such as cotton linters, rayon, polyester, nylon, acrylic or the like, having a length of from about 0.64 cm to about 1.91 cm, preferably about 1.27 cm and a denier of from about 1.0 to 5 and present in an amount from about 2 to about 20% by weight, most preferably from about 2% to about 6%.

The slurry is sheeted onto a Fourdrinier wire and dewatered to form a starting sheet. The slurry may range from about 0.1% to about 1% solids by weight and other ingredients may be added to the slurry such as, for example, colouring agents, wetting agents, adhesives, or the like. After laying the slurry on the Fourdrinier wire, initial dewatering may take place under the influence of vacuum to render the water content to about 5 parts by weight of water per part by weight of solids.

The density of the sheet may be controlled by varying such factors as the pressure difference during the vacuum dewatering and the speed of the Fourdrinier wire. Generally, decreased vacuum and increased speed will result in a less dense product. A suitable low density sphagnum moss board can be produced with a sheet lay down of from about 160 to about 375 grams of solid per square meter of the sheet and for a vacuum pressure of from 19 millimeters of mercury (mmHg) to 28 mmHg. The speed of the Fourdrinier wire and the width of the vacuum slot under which the sheet is exposed to the pressure differential of the vacuum should be varied so as to create a residence time of the sheet over the vacuum slots of about 1 to about 5 seconds. For example, with 2 slots each having a 2.5 cm width, a Fourdrinier wire speed of about 0.76 meters per minute results in a residence time of about 1.5 seconds which, with a lay down of 215 grams per square meter, produces a low density board. Similarly, with 4 slots, each with a 2.5 cm width, a Fourdrinier speed of 0.52 meters per minute results in a residence time of 4.4 seconds and also produces a low density sphagnum moss sheet. In each of the above examples, a vacuum of about 22.5 mmHg.

Irrespective of the choice of parameters chosen, the resulting sheet, prior to calendering is of low density, generally from about 0.04 to about 0.12 gm/cm$^2$.

In a specific embodiment of this invention, a laminate is made from the sheet and a reinforcing layer of Kraft wood pulp. Preferably, the Kraft wood pulp is first laid down on a Fourdrinier wire from a slurry which can be about 0.1% solids by weight. The Kraft slurry is dewatered and then passes to a second station where the sphagnum moss and additives is laid directly on top of the Kraft layer. This composite layer may be dewatered to produce a laminate of the low density sphagnum moss sheet described herein having a layer of Kraft pulp adhered to its surface. The strength characteristics of such laminate are greater than that which would result when the sphagnum moss board is used alone. It is preferred that the Kraft employed be bleached and have a Canadian Standard Freeness of relatively high value, e.g. about 450 to 750. While the proportions of the Kraft layer to the sphagnum moss are not critical, a suitable product results when the layer of about 5.5 to 54 grams of Kraft wood pulp per square meter is employed.

If desired, a Kraft wood pulp layer may also be laid on top of the sphagnum moss layer to form a sandwich-like structure comprising a central sphagnum moss core covered by two layers of Kraft wood pulp. This form of construction further enhances the strength characteristics of the final sheet.

The resulting laminate is dried and then calendared in order to increase its drying power. FIG. 5 illustrates the structure of such laminate, designated comprehensively by the reference numeral 10. Reference 12 designates the sphagnum moss layer, while references 14 and 16 identify the reinforcing Kraft wood pulp layers.

In order to increase the comfort potential of the structurally integral sheet, the calendaring operation is followed by mechanical working such as perf-embossing or microcorrugating. These treatments are well-known to persons skilled in the art and have the effect of tenderizing the sheet for the purpose of reducing its stiffness.

The tenderized sheet forms an absorbent core suitable for use in a disposable absorbent product such as sanitary napkins, diapers, urinary pads, adult briefs, wound dressings and the like. An exemplary representation of a sanitary napkin incorporating an absorbent sheet in accordance with the invention is shown in FIG. 6. The sanitary napkin comprehensively designated by the reference numeral 18 includes an absorbent core formed by the structurally integral absorbent sheet 10 in accordance with the invention. The absorbent core is mounted in a jacket formed by a body-contacting, liquid-pervious layer 20 and a liquid-impervious layer 22 to prevent body exudate from egressing the garment facing surface of the sanitary napkin 18.

The scope of the present invention is not limited by the description, examples and suggestive uses herein, as modifications can be made without departing from the spirit of the invention. Applications of the product and the methods of the present invention for sanitary and other health-care uses can be accomplished by any sanitary protection, incontinence, medical and absorbent methods and techniques as are presently or prospectively known to those skilled in the art. Thus, it is intended that the present application covers the modifications and variations of this invention provided that they come within the scope of the appended claims and their equivalents.

We claim:

1. A liquid-absorbent article primarily having an absorbent core wherein said core contains substantially pure, undecomposed particles of sphagnum moss plants that belong to one species selected from the group consisting of:

1) all species from the botanical section ACUTIFOLIA;

2) all species from the botanical section RIGIDA;

3) all species from the botanical section SUBSECUNDA;

4) all species from the botanical section CUSPIDATA;

5) *Sphagnum centrale, Sphagnum erythrocalyx, Sphagnum henryense, Sphagnum perichaetiale, Sphagnum portoricence* from the botanical section PALUSTRIA.

2. A liquid-absorbent article having an absorbent core wherein said core contains primarily substantially undecomposed particles of sphagnum moss plants that belong to at least one species selected from the group consisting of:

1) all species from the botanical section ACUTIFOLIA;

2) all species from the botanical section RIGIDA;

3) all species from the botanical section SUBSECUNDA;

4) all species from the botanical section CUSPIDATA;

5) *Sphagnum centrale, Sphagnum erythrocalyx, Sphagnum henryense, Sphagnum perichaetiale, Sphagnum portoricence* from the botanical section PALUSTRIA, said structurally integral liquid-absorbent product having an absorbency performance index in the range from about 1 to about 4.

3. A liquid-absorbent article having an absorbent core wherein said core contains primarily a composition of substantially undecomposed sphagnum moss, said composition having a major fraction constituted by at least one species that belongs to the botanical section PALUSTRIA and a smaller fraction including one or more sphagnum moss species selected from the botanical sections group consisting of ACUTIFOLIA, RIGIDA, SUBSECUNDA and CUSPIDATA.

4. A liquid-absorbent product as defined in claim 3 wherein said composition has an absorbency performance index in the range from about 1 to less than 4.

5. A disposable absorbent product, comprising:
an absorbent core including primarily substantially undecomposed particles of sphagnum moss plants that belong to at least two botanical sections selected from the group consisting of PALUSTRIA, ACUTIFOLIA, RIGIDA, SUBSECUNDA and CUSPIDATA, said absorbent core having an absorbency performance index in the range from about 1 to less than 4; and
a body contacting, liquid-pervious layer superposed to said absorbent core.

6. A disposable absorbent product as defined in claim 5, further comprising a liquid-impervious layer underneath said absorbent core for preventing fluid captured by said absorbent core to egress said absorbent product.

7. A disposable absorbent product as defined in claim 5, wherein said product is selected from the group consisting of sanitary napkin, diaper, adult incontinence brief, urinary pad and wound dressing.

8. A liquid-absorbent article comprising an absorbent core containing primarily substantially undecomposed particles of sphagnum moss plants that belong to at least two botanical sections which are selected from the group consisting of PALUSTRIA, ACUTIFOLIA, RIGIDA, SUBSECUNDA and CUSPIDATA, said absorbent core having an absorbency performance index in the range from about 1 to less than 4, and a body contacting, liquid pervious layer superposed to said absorbent core.

9. A liquid-absorbent article as defined in claim 8, wherein said absorbency performance index is in the range from about 2 to less than 4.

10. A liquid-absorbent article as defined in claim 8, wherein said absorbency performance index is in the range from about 3 to less than 4.

11. A liquid-absorbent article as defined in claim 8, wherein said product includes a component selected from the group consisting of rayon, polyester, nylon, acrylic, Kraft wood pulp, mechanical wood pulp, cotton linters and mixtures thereof.

12. A liquid-absorbent article as defined in claim 8, wherein the absorbent core is a structurally integral sheet.

13. A liquid-absorbent article as defined in claim 8, wherein said product is mechanically tenderized for increasing a softness and flexibility of said product.

14. A liquid-absorbent article as defined in claim 13, wherein said product is mechanically tenderized by a method selected from the group consisting of perf-embossing and microcorrugating.

15. A liquid-absorbent article as defined in claim 8, wherein said product is in the form of a sheet.

16. A liquid-absorbent article as defined in claim 15, wherein said product has a laminated structure including a reinforcing layer to enhance a structural integrity of said product.

17. A liquid-absorbent article as defined in claim 16, wherein said reinforcing layer includes Kraft wood pulp fibers.

18. A liquid-absorbent article as defined in claim 16, wherein said reinforcing layer forms an outer surface of said product.

19. A liquid-absorbent article as defined in claim 1, wherein said product includes an absorbent layer containing said particles of sphagnum moss plants, said absorbent layer being united with said reinforcing layer, said reinforcing layer being made of fibrous material.

20. A liquid-absorbent article as defined in claim 19, wherein said product includes a pair of reinforcing layers of fibrous material in a spaced apart relationship, said absorbent layer being mounted between said reinforcing layers of fibrous material.

* * * * *